(12) United States Patent
Johnson et al.

(10) Patent No.: US 6,203,511 B1
(45) Date of Patent: Mar. 20, 2001

(54) ORTHOTIC JOINT AND METHOD

(75) Inventors: James A. Johnson, Lake Orion, MI (US); Robin W. McCall, Tryon, NC (US)

(73) Assignee: Becker Orthopedic Appliance Company, Inc., Troy, MI (US)

( * ) Notice: Subject to any disclaimer, the term of this patent is extended or adjusted under 35 U.S.C. 154(b) by 0 days.

(21) Appl. No.: 09/105,032

(22) Filed: Jun. 25, 1998

(51) Int. Cl.⁷ .................................................. A61F 5/00
(52) U.S. Cl. .................... 602/16; 602/5; 602/20; 602/23
(58) Field of Search .................... 602/5, 12, 16, 602/20, 23, 26, 27; 482/144, 909; 403/92, 93, 113, 116

(56) References Cited

U.S. PATENT DOCUMENTS

| | | | |
|---|---|---|---|
| 4,738,252 | * | 4/1988 | Friddle et al. ............... 602/16 |
| 5,421,810 | * | 6/1995 | Davis et al. ................. 602/16 |
| 5,571,078 | | 11/1996 | Malewicz .................... 602/27 |
| 5,921,946 | * | 7/1999 | Tillinghast .................. 602/16 |
| 5,938,629 | * | 8/1999 | Bloedau ...................... 602/16 |

* cited by examiner

Primary Examiner—Kim M. Lee
(74) Attorney, Agent, or Firm—Ryndak & Schwartz

(57) ABSTRACT

A mechanical joint for pivotally connecting two members, particularly members of an orthopedic or orthotic device, to limit the degree of pivotal movement between the members and precisely and easily adjust the position of limited pivotal movement between the two members.

29 Claims, 4 Drawing Sheets

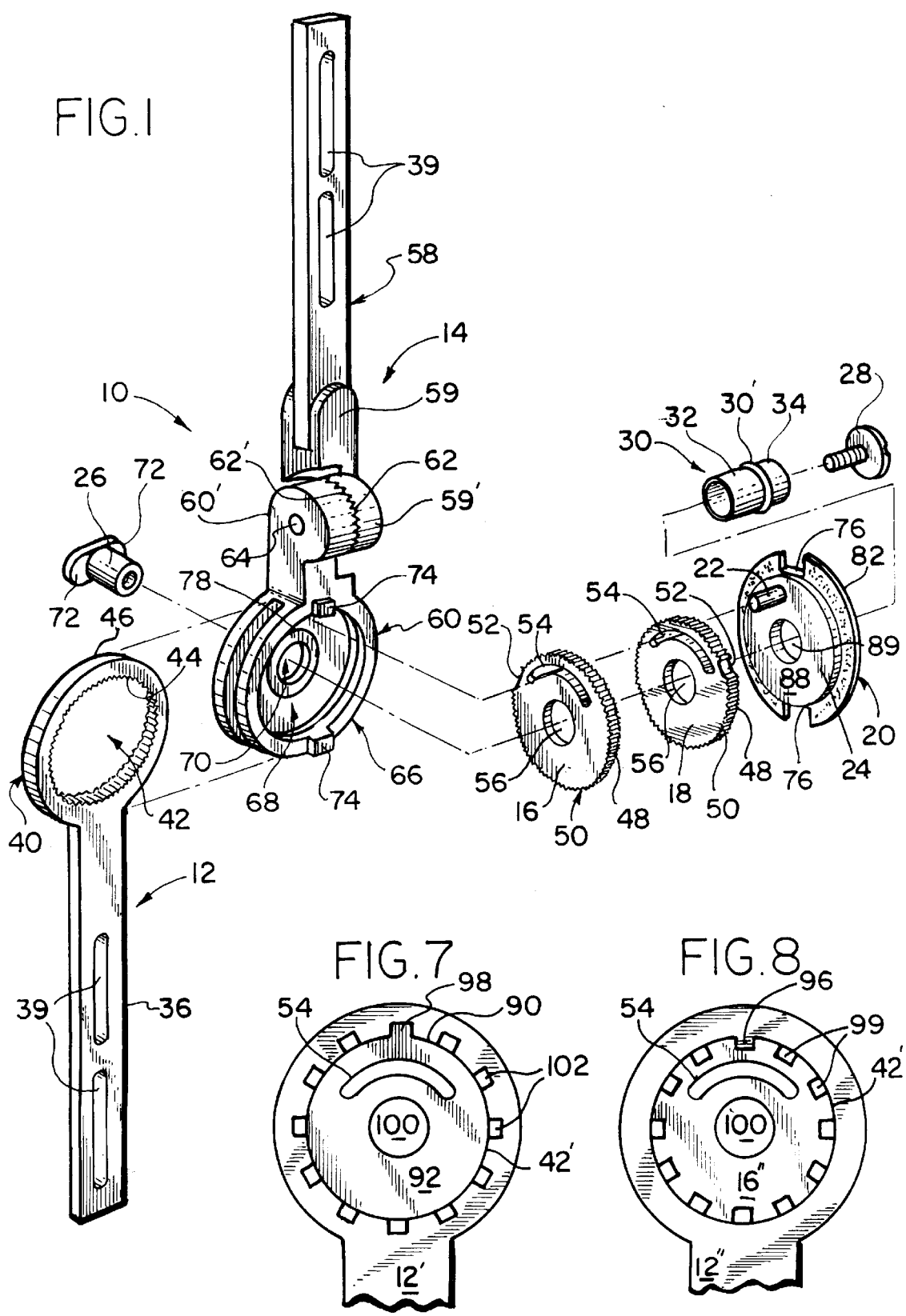

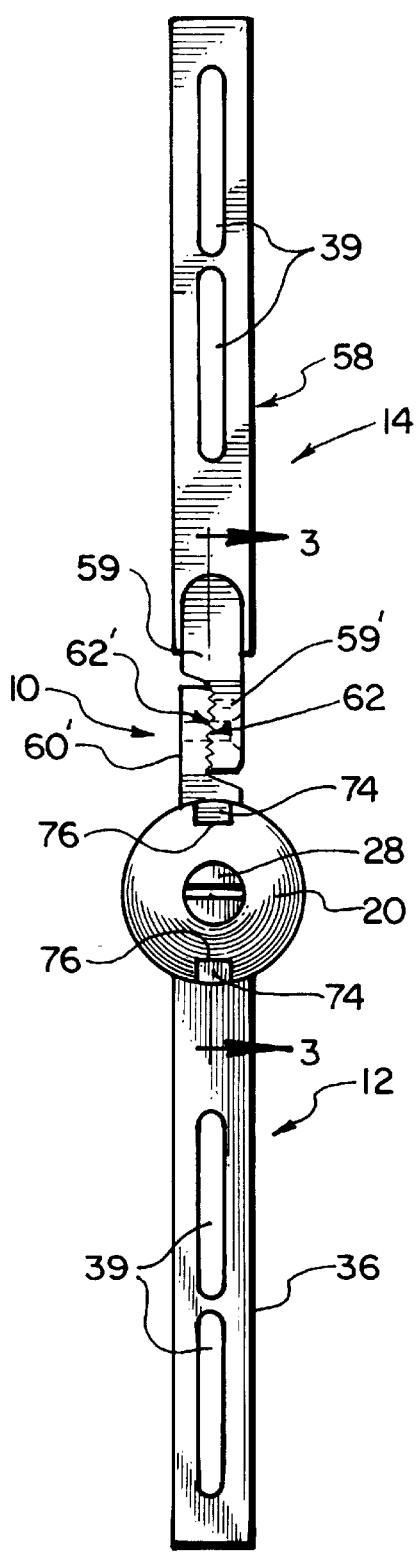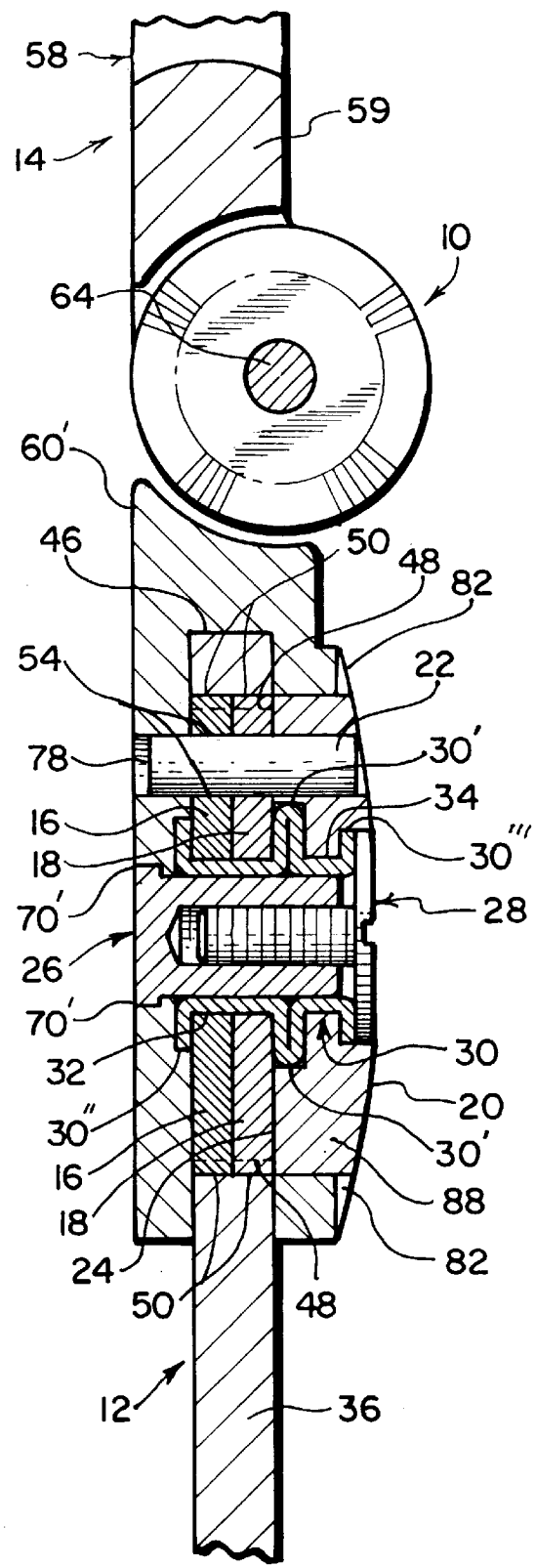

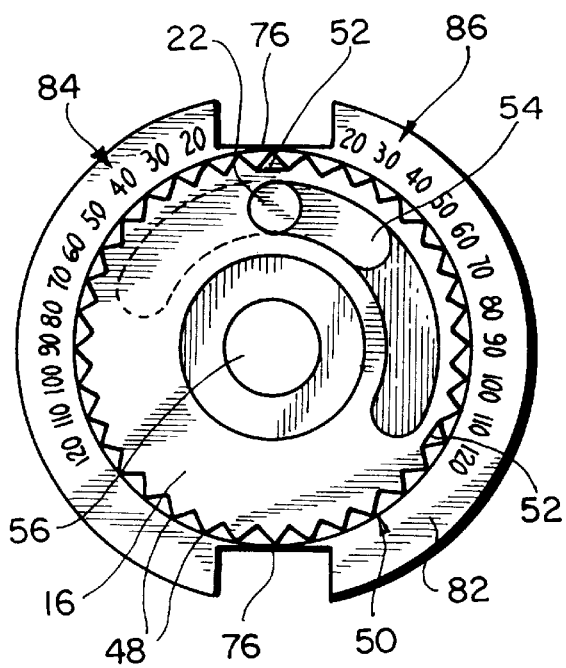
FIG. 4
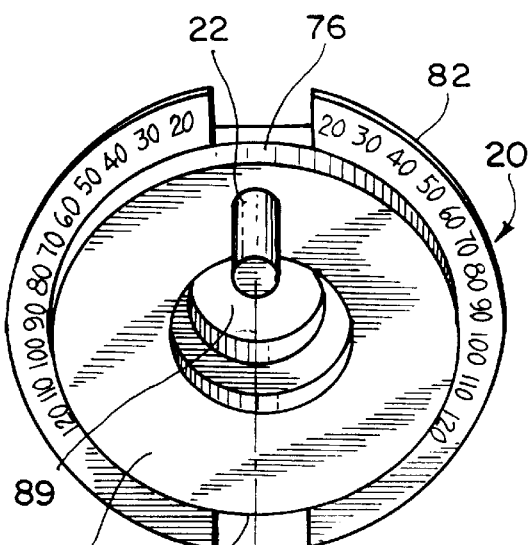
FIG. 6
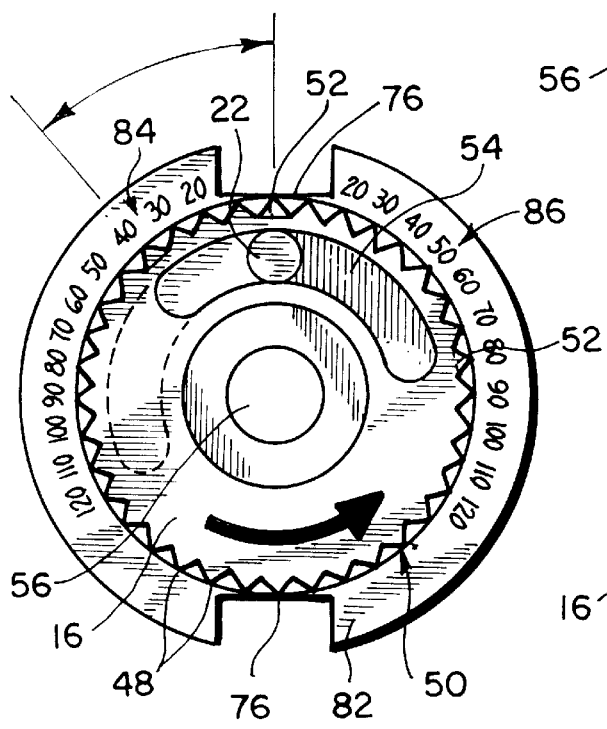
FIG. 5
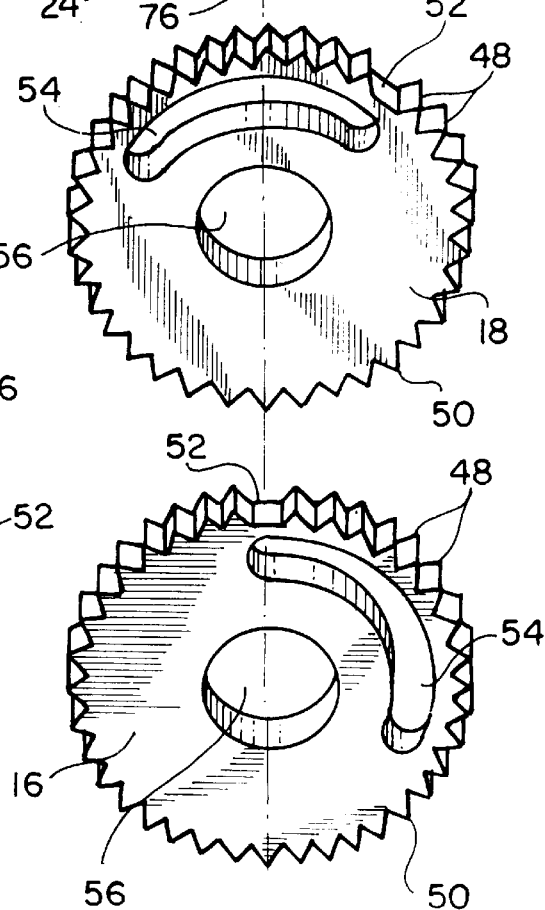

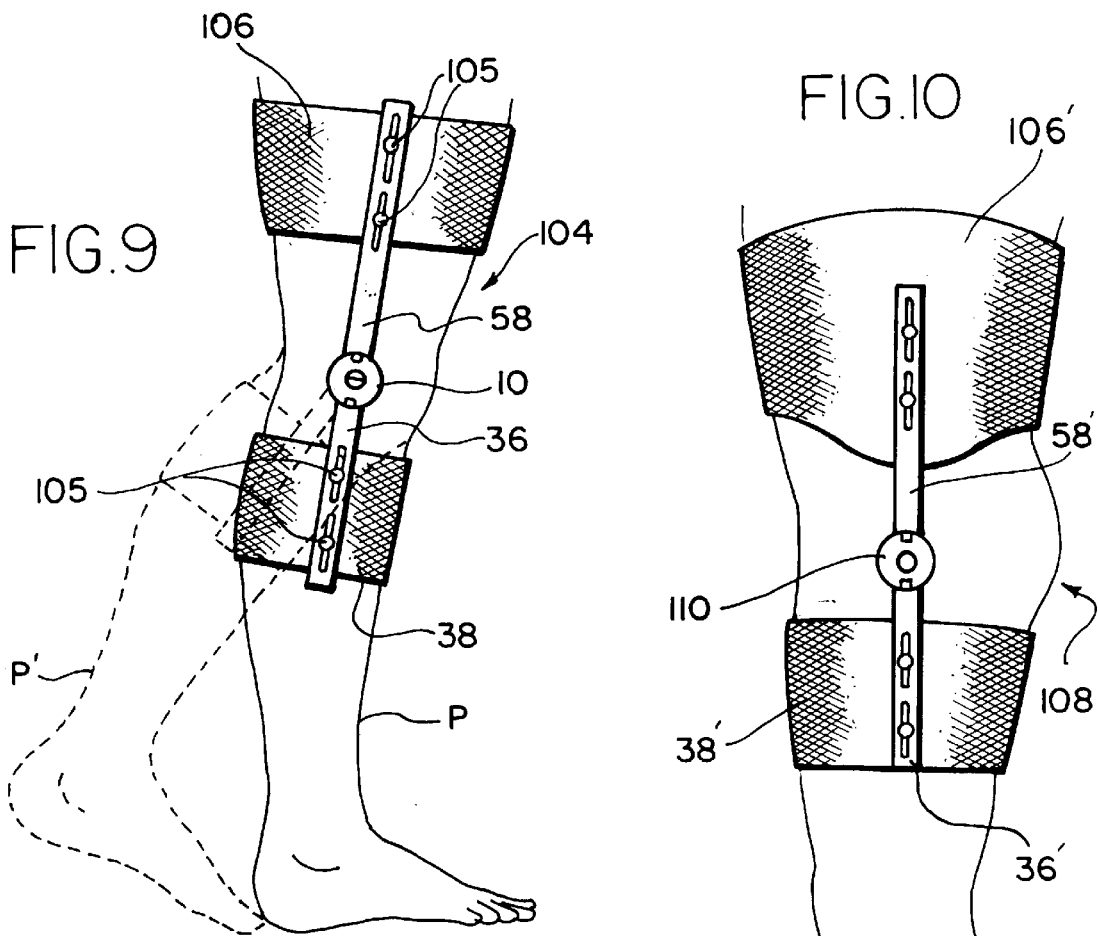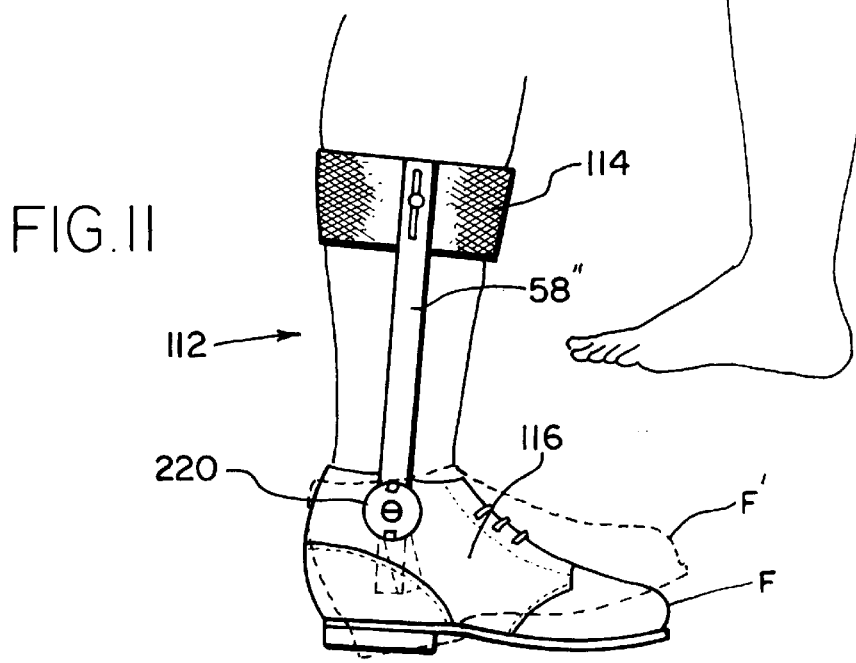

ORTHOTIC JOINT AND METHOD

FIELD OF THE INVENTION

This invention relates to a mechanical joint for pivotally connecting two members of an orthotic device to limit pivotal movement of the two members. More particularly, the invention relates to a mechanical joint particularly suited to connecting two members of an orthopedic or orthotic appliance to control the degree and position of pivotal movement of the two members and the corresponding parts of the human body to which the members are attached within a preselected and adjustable range of pivotal movement.

BACKGROUND OF THE INVENTION

Orthotic devices have traditionally been utilized to aid in support, guiding and limiting the range of motion of different joints in the human body. A mechanical joint is frequently used to pivotally connect two orthotic members secured to the body above and below the joint which members form part of the orthotic appliance, mounted on opposite ends such as for attachment to the foot, leg, arm, hand or neck of the body. Such a mechanical joint permits and controls relative movements of the members and the corresponding body parts to which the members are attached and the body joint to which the body parts are connected. Portions of orthotic devices have been constructed with thermoplastic resins or other materials and are conformed to the shape of an individual patient's anatomy. In a typical ankle-foot orthotic device, a plastic molded member of the orthotic device is conformed to the lower ankle and plantar region of the foot. This plastic member is pivotally connected to a second molded plastic member that is conformed to the shape of the rear lower leg and calf of the patient. These two members are connected pivotally at their sides adjacent to the ankle of the patient by use of mechanical joints to provide lateral support for the lower leg, ankle and foot of patients. This orthotic device permits pivotal movement of a desired part of the body through only a limited set range of flexion and extension.

One such prior art mechanical joint construction consists of a pivotably connected metal disc and plate disclosed in U.S. Pat. No. 4,738,252. The disc is provided with an arcuate slot radially spaced from the pivot point of the disc. A protrusion on the disc extends into the slot and moves there along to limit the relative rotation between the disc and the plate and the relative pivotal movement of the two members of the orthotic device. The orthotic device correspondingly limits the degree of flexion and extension of the foot relative to the lower leg of the patient.

A need exists for an orthotic device which can be easily adjustable to set the degree of pivotal movement permitted by the orthotic device about the orthotic joint thereof over a range without requiring additional orthotic device parts or changing parts to provide the desired degree of pivotal movement. A need also exists for such an orthotic joint that has few parts and is simple and economical in construction.

SUMMARY OF THE PRESENT INVENTION

In accordance with the present invention, a mechanical joint for connecting two members for limited relative pivotal motion or movement is provided that may be easily adjustable for a range of pivotal orthotic joint movement from 0° to 180° or more. The inventive joint is especially useful for a hip orthosis (to control hip flexion and extension). Another aspect of the present invention is to provide a mechanical orthotic joint which uses two cooperating disc members, each of which has a curved slot radially spaced from the axis of rotation and extending through the side thereof that overlap to provide the desired degree of orthotic joint pivotal movement. The amount of overlap of the curved slots defines an effective slot length that determines the extent of permitted pivotal movement and such overlap can be easily and quickly adjusted by changing the degree of slot overlap between the two disc members.

In accordance with another aspect of the invention, the desired range of motion can be easily and quickly adjusted as the patient circumstances change to permit greater or lesser degrees of pivotal orthotic joint movement. In addition, visible markings or indicia of the range of permitted flexion and extension are provided to facilitate accurate and simple adjustment of the permitted pivotal movement of the orthotic device. The present invention also provides a mechanical joint that is relatively simple to assemble, reliable and economical. This construction in one embodiment is achieved by a novel fork-like member that forms a portion of the joint and provides structure for the mounting of the cooperating disc members in a fixed relation. The structure cooperates with the discs to permit them to be mounted in fixed relation in a plurality of predetermined relative positions to be chosen by the orthotist, for example, with respect to each other and the fork-like member.

In accordance with another aspect of the present invention, an orthotic joint for pivotally connecting two orthotic members is provided. The joint includes a pair of cooperating discs, each disc having a curved slot which is radially spaced from the axis of rotation of each slot. The slot extends through the disc. In operation, the extent of slot overlap defines a permitted range of pivotal movement of the joint. Structure is provided for adjustably and removably mounting the discs in fixed relation to each other to define the slot overlap. Structure is also provided for mounting the discs in fixed relation to one of the orthotic members. In addition, structure is provided for pivotally traversing the slot overlap of the discs and that structure is mounted in fixed relation to the other orthotic member.

In accordance with one aspect of the invention, the structure for adjustably and removably mounting the discs in fixed relation to each other includes a plurality of outwardly extending teeth spaced apart on the periphery of each of the discs and a plurality of corresponding teeth spaced apart around the periphery of an opening in a member that is fixed relative to the first of said orthotic members with the opening permitting the discs to be mounted therein.

In accordance with another aspect of the present invention, the other orthotic member has a joint end that comprises a clevis, the clevis dimensioned to permit the structure for mounting the discs to be contained between the clevis. Generally, the slots will have a radial extent of at least about 120°, allowing the discs to be adjusted to provide a slot overlap of from about 0° to about 120°.

In accordance with another aspect of the present invention, an orthosis is provided that includes the orthotic joint in accordance with the invention.

In accordance with still another aspect of the present invention, a method of adjusting an orthotic joint to provide the desired range of pivotal movement in the joint is provided. The joint is of the type that is in accordance with the invention and the method includes adjusting the relative relationship of the discs to provide a desired degree of slot overlap which corresponds to the desired range of pivotal movement of the joint and installing the discs while in that relative relationship in the structure for containing the discs to provide the desired range of pivotal joint movement.

BRIEF DESCRIPTION OF THE DRAWINGS

FIG. 1 is a perspective exploded view of an orthotic joint of the present invention;

FIG. 2 is a side elevation view of the orthotic joint of FIG. 1;

FIG. 3 is a sectional view of the orthotic joint along line 3—3 of FIG. 2;

FIG. 4 is a side elevation view of a portion of the orthotic joint of the present invention;

FIG. 5 is a side elevation view of a portion of the orthotic joint of FIG. 4 with the inner and outer discs rotated by 40 degrees relative to the scale;

FIG. 6 is a perspective exploded view of the portion of the orthotic joint of FIG. 4;

FIG. 7 is a side elevation view of a portion of an orthotic joint of an alternative embodiment of the present invention;

FIG. 8 is a side elevation view of a portion of the orthotic joint of another embodiment of the present invention;

FIG. 9 is a perspective view of a knee orthotic device in accordance with the present invention;

FIG. 10 is a perspective view of a hip orthosis in accordance with the present invention; and FIG. 11 is a perspective view of an ankle orthotic device in accordance with the present invention.

DETAILED DESCRIPTION OF THE INVENTION

Referring to the figures generally, and in particular to FIGS. 1–3, there is illustrated an adjustable mechanical orthotic joint 10 in accordance with the present invention. Orthotic joint 10 is particularly usefull for connecting two orthotic members together for limited relative pivotal movement with respect to those members in which the degree of limited pivotal movement can be set by the user or orthotist at a desired range of motion. In addition, orthotic joint 10 can be easily adjusted to provide a different range of pivotal motion quickly and easily and without replacing any parts.

Although sometimes described in detail herein with respect to a knee orthosis, the mechanical orthotic joint of the present invention is applicable to ankle (to control/limit ankle plantar flexion and ankle dorsiflexion), elbow and neck orthotic devices and is particularly usefill as a hip orthosis incorporating a thigh cuff and a pelvic section, as well as any other situation where limiting the relative pivotal movement of two orthotic members is desired.

Adjustable mechanical orthotic joint 10 is composed of a plurality of cooperating components including a first elongated member 12, an elongated clevis-like member 14, a pair of cooperating discs 16 and 18, a cover plate 20 having a pin or finger 22 projecting inwardly from interior surface 24, an interior threaded bushing 26 and complementary fastening member 28 and a flanged bushing 30 which provides bearing surfaces 32 and 34 as hereinafter described.

First elongated member 12 includes an elongated portion 36 that permits attachment to an orthotic cuff 38 as illustrated in FIG. 9, for example. A pair of slots 39 are provided for facilitating attachment to orthotic cuff 38. Alternatively, holes or other suitable structure for readily permitting attachment of member 12 to an orthotic cuff or other portion of an orthotic device can be utilized, as is well known to those skilled in the art.

One end of first elongated member 12 terminates at a joint end 40 and has a relatively large circular opening 42 to accommodate and rigidly secure therein discs 16 and 18, as hereinafter described. The outer portion 46 of joint end 40 of elongated member 12 is preferably circular. Circular opening 42 has a plurality of inwardly extending serrations or gear teeth 44 that are complementary to the outwardly extending gear teeth or serrations of discs 16 and 18 as hereinafter described. Any suitable structure, whether meshing or otherwise can be provided to rigidly secure discs 16 and 18 therein.

In the illustrated embodiment, first elongated member 12 forms the lower portion of orthotic joint 10 and elongated portion 36 can be considered as the lower portion of the orthosis as hereinafter described.

Discs 16 and 18 are circular, having a plurality of outwardly extending gear teeth or serrations 48 on circular edge 50. Indicia 52 provides a visual indication of the location of slots 54 of discs 16 and 18. Indicia 52 may be provided on circular edge 50 to provide a reference to allow the orthotist or user to determine the orientation of discs 16 and 18 as hereinafter described. Indicia 52 can be of any suitable form such as a marking, line or raised portion and in this case is the absence of one gear tooth as shown in FIG. 1.

In the illustrated embodiment, discs 16 and 18 are identical and each includes a curved slot 54 spaced radially from the axis of rotation and located near the peripheral circular edge 50. Slots 54 are of a width sufficient to accommodate finger 22 as hereinafter described. Slots 54 should be of sufficient radial extent relative to circular edge 50 to at least be equal to or greater than the maximum extent of pivotal motion that is desired. Slots 54 could extend substantially around the entire radial extent of discs 16 and 18. In the illustrated embodiment, slots 54 have approximately a 120° radial extent.

Discs 16 and 18 are dimensioned to cooperatively fit within circular opening 42 of first elongated member 12 in fixed relationship by virtue of intermeshing of gear teeth 44 and 48 as shown in FIGS. 1 and 3.

Each of discs 16 and 18 have a central aperture 56 that defines the axis of rotation and is dimensioned to receive flanged bushing 30 in a frictional fit relationship, as illustrated in FIG. 3. In this manner, bushing 30 provides bearing surface 34 for discs 16, 18 and cover plate 20 as hereinafter described.

Clevis-like member 14 forms a portion of the upper part of the orthotic devices illustrated in FIGS. 9–11 and includes an upper elongated portion 58 that is attached to lower terminal clevis portion 60. Elongated portion 58 has a pair of slots 39 therein to facilitate mounting to an orthotic cuff. Elongated portion 58 terminates and is mounted in a slotted member 59 which has a lower portion 59' that adjustably couples to upper clevis portion 60' by means of complementary tooth surfaces 62 of member 59 and 62' of upper clevis portion 60' held together by means of a threaded fastener 64. Such structure permits elongated portion 58 to be angled inwardly or outwardly as required to properly fit the upper limb of a patient. Similar structure could be provided in connection with first elongated member 12, if desired.

Clevis 66 is spaced a distance sufficient to just accommodate the thickness of joint end 40 of first elongated member 12 as shown in FIGS. 1 and 3. One side of clevis 66 has a large opening 68 to permit insertion therethrough of discs 16 and 18 into and in intermeshing engagement with circular opening 42 of first elongated member 12. Discs 16 and 18 are aligned in a predetermined position relative to each other when inserted in intermeshing engagement in circular opening 42 to provide the desired range of pivotal movement of orthotic joint 10, as hereinafter described in detail. The other side of clevis 66 has a small opening 70 sufficient to just accommodate interior threaded bushing 26. As will be appreciated, small opening 70 could be larger, if desired. Adjacent small opening 70 is a recessed area 70' that corresponds in shape to outwardly extending tabs 72 of interior threaded bushing 26 which prevent relative movement of bushing 26 when inserted in position through opening 70.

The top and bottom portions of adjacent large opening 68 of clevis portion 60 includes a pair of raised portions 74 having a width slightly less than slots 76 of cover plate 20 to prevent relative movement of cover plate 20 relative to clevis-like member 14. In addition, the side of clevis 66 portion having small opening 70 includes an aperture 78 to permit insertion of finger 22 therein to also prevent relative movement of cover plate 20 relative to clevis-like member 14. Consequently, aperture 78 is only slightly larger than the diameter of finger 22.

Two separate rings (not shown) could be used in place of clevis 66 which would be rigidly mounted in some manner to elongated portion 14.

After discs 16 and 18 are inserted through large opening 68 and into intermeshing relationship with circular opening 42, cover plate 20 is then fixed in position in orthotic joint 10 by inserting finger 22 through slots 54 of discs 16 and 18 and then into aperture 78.

Cover plate 20 includes a centrally disposed aperture 89 that permits a combination therein of threaded bushing 20, and flanged bushing 30 so that cover plate 20 bears on bearing surface 34 of bushing 30 and discs 16 and 18 bear on bearing surface 32 with flange 30' separating bearing surfaces 32 and 34. The ends 30" and 30'" of bushing 30 are flared out slightly after discs 16 and 18 and cover plate 20 are mounted thereon as shown in FIG. 3. Cover plate 20 includes finger 22 which is rigidly secured thereto and can be provided as a separate piece which can be press fit into an aperture (not shown) located in cover plate 20 or finger 22 can form an integral part of cover plate 20, for example.

Cover plate 20 has a flange 82 in which slots 76 are located. On the inner surface of flange 82 are located right flexion and left flexion degree scales 84 and 86, respectively, as shown in FIGS. 4–6. Degree scales 84 and 86 permit easy adjustment to the desired maximum permitted angle of flexion and extension the patient by the orthotist, for example.

Cover plate 20 includes a circular body portion 88 which is dimensioned for insertion through large opening 68 of lower terminal clevis portion 60. Body portion 88 has a central aperture 89 therethrough.

Adjustment and operation of orthotic joint 10 will now be described, particularly with respect to FIGS. 4–6 and 9–11.

Turning now to FIGS. 4 and 6, there are illustrated certain components of the present invention, including outer disc 18, inner disc 16 and cover plate 20 in assembled relation. As shown in the Figures, including FIG. 1 circular edges 50 of discs 16 and 18 intermesh with corresponding circular opening 42 when placed in position therein to securely maintain in position and prevent relative movement of discs 16 and 18 relative to first elongated member 12. Finger 22 is received in the curved slots 54 of inner disc 16 and outer disc 18. By removing discs 16 and 18 from opening 42 and then rotating inner disc 16 and outer disc 18 relative to each other and/or relative to cover plate 20 and then replacing discs 16 and 18 in the desired orientation in opening 42, the overlap and/or radial position of curved slots 54 is changed. This, in turn, determines the degree of permitted pivotal movement for the patient (or radial position of movement). The degree of slot overlap of slots 54 of discs 16 and 18 (which becomes fixed when discs 16 and 18 are placed in position and secured in opening 42) determines the permitted extent of radial or pivotal movement of joint 10 and the relative relation of discs 16 and 18 to cover plate 20 and first elongated member 12 determines the orientation for that extent of pivotal movement.

For example, in one embodiment of the present invention, curved slots 54 may be of identical dimensions, such as an arc of 120 degrees. Curved slots 54 may also completely overlap and be positioned with respect to plate 20 to provide the maximum degree of pivotal movement (i.e., 120° flexion). In such example, finger 22 limits the range of motion between the ends of both openings to zero to one hundred twenty degrees for flexion. As shown in FIG. 4, discs 16 and 18 are set for 40° of right flexion.

As shown in FIG. 5, if outer disc 18 is then rotated about 40 degrees counterclockwise relative to cover plate 20 (cover plate 20 is not rotated), then the range of allowed motion for orthotic joint 10 will be changed to about 40° of left flexion. Accordingly, by rotating inner disc 16 or outer disc 18 relative to each other, numerous different ranges of flexion or extension can be provided without using additional or changing parts of joint 10. By providing finer serrations or teeth 44 and 48, the range of movement can be more finely adjusted.

Turning to FIG. 7, there is illustrated an alternative embodiment of the present invention. Circular periphery 90 of inner disc 92 and circular periphery of outer disc (not shown) each have a notch or key 98 and a central aperture 100 and a slot 54. Notch or key 98 on disc 92 and the outer disc may be in different positions with respect to each other. Opening 42' on member 12' has a plurality of keyways 102 complementary to notch 98 for securely receiving notch 98 in a desired one of keyways 102 and for preventing relative movement of disc 92 and outer disc relative to member 12' in place of teeth 44 (member 12' otherwise corresponds to member 12). Additionally, as illustrated in FIG. 8, another alternative embodiment of the invention utilizes a key 96 in opening 42' of member 12" and a plurality of keyways 99 located around the periphery of inner disc 16" and the outer disc (not shown), each having an aperture 100 and a slot 54.

It will be understood that discs 16 and 18 and member 12 can be otherwise modified to incorporate any structure which permits adjustment and secures such modified discs to a modified first member in fixed relationship can be used in accordance with the invention. For example, discs 16 and 18 and member 12 could be toothless and discs could be secured to member 12 by means of a set screw (not shown) extending through holes normal to the periphery of circular edges 50 and outer portion 46, for example. Alternatively, one disc could utilize one type of mounting structure and the other disc could utilize another type of mounting structure.

Turning now to FIGS. 9, 10 and 11, there are illustrated various orthotic devices for different parts of the body embodying the present invention. FIG. 9 depicts a knee orthotic device 104 incorporating joint 10 worn by a patient P. Upper elongated portion 58 is attached to plastic orthotic cuff 106 by threaded fasteners 105 or any other suitable means. Cuff 106 may be leather or a plastic contoured piece. Joint 10, in accordance with the present invention and as previously described, may be adjusted to allow the patient varying degrees of limited pivotal movement as illustrated by position P'. Lower elongated portion 36 is also attached to plastic cuff 38 by threaded fasteners 105 or any other suitable means.

FIG. 10 illustrates a hip orthosis 108. Specifically, upper elongated portion 58' and lower elongated portion 36' are connected to pelvic section 106' and thigh cuff 38', respectively. Hip orthosis joint 110, similar in construction to joint 10, is connected to elongated portions 58' and 36' in a manner similar to orthotic device 104.

FIG. 11 illustrates an ankle orthosis 112 composed of a joint 220 similar in construction to joint 10. Elongated portion 58", similar to elongated portion 58, is attached to cuff 114 and joint 220. Joint 220 is connected to foot engaging member 116 for allowing limited pivotal movement of foot F to position F'.

While the invention has been described with respect to certain preferred embodiments, as will be appreciated by those skilled in the art, it is to be understood that the invention is capable of numerous changes, modifications and rearrangements, and such changes, modifications and rearrangements are intended to be covered by the following claims.

We claim:

1. An orthotic joint for pivotally connecting two orthotic members, comprising:
   (a) a pair of cooperating discs each having an axis of rotation, a periphery and, each disc having a curved slot radially spaced from the axis of rotation, at least a portion of each curved slot overlapping, the extent of slot overlap defining a permitted range of pivotal movement of said joint;
   (b) means for adjustably and removably mounting said discs in fixed relation to each other to define the slot overlap in a fixed position;
   (c) means for mounting said discs in fixed relation to one of the orthotic members; and
   (d) structure for pivotally traversing the slot overlap, said structure mounted in fixed relation to the other orthotic member.

2. The orthotic joint of claim 1 wherein said means for adjustably and removably mounting said discs in fixed relation to each other comprises a plurality of outwardly extending teeth spaced apart on the periphery of each of said discs and a plurality of corresponding teeth spaced apart around the periphery of an opening in a member that is fixed relative to said one of said orthotic members, said opening permitting said discs to be mounted therein.

3. The orthotic joint of claim 2 wherein said plurality of outwardly extending teeth extends around substantially the entire periphery of each disc.

4. The orthotic joint of claim 1 wherein said structure for traversing the slot overlap comprises a pin.

5. The orthotic joint of claim 1 wherein said other orthotic member has a joint end that comprises a clevis, the clevis dimensioned to permit said means for mounting said discs to be contained between said clevis.

6. The orthotic joint of claim 5 wherein one side of said clevis has an opening sufficiently large to permit insertion of said discs therethrough.

7. The orthotic joint of claim 6 wherein said structure for traversing the slot overlap comprises a pin.

8. The orthotic joint of claim 7 wherein said pin is rigidly mounted to a cover plate that is rigidly affixed and restrained from movement relative to said other orthotic member.

9. The orthotic joint of claim 8 wherein said cover plate has indicia on at least one side thereof to identify a range of pivotal movement of said joint.

10. The orthotic joint of claim 8 further comprising at least one slot located at the periphery of said cover plate and a corresponding raised portion adjacent said large clevis opening to prevent movement of said cover plate relative to said clevis.

11. The orthotic joint of claim 10 wherein said joint can be adjusted to provide from about 0° to about 120° of flexion.

12. The orthotic joint of claim 1 further comprising indicia on at least one of said discs to provide a visual indication of the location of the slot of said disc.

13. The orthotic joint of claim 1 wherein said slots each have a radial extent of at least about 120° and said discs can be adjusted to provide a slot overlap from about 0° to about 120°.

14. The orthotic joint of claim 1 wherein said means for adjustably and removably mounting said discs in fixed relation to each other and for mounting said discs in fixed relation to one of the orthotic members comprises a key in one of said means for mounting said pair of discs and a plurality of keyholes in the other of said means for mounting said pair of discs.

15. The orthosis of claim 1 further comprising indicia on at least one of said discs to provide a visual indication of the location of the slot of said disc.

16. An orthosis comprising:
   (a) upper and lower orthotic members;
   (b) a pair of cooperating discs, each disc having a curved slot, at least a portion of each curved slot overlapping, the extent of slot overlap defining a permitted range of pivotal movement of said joint;
   (c) means for adjustably and removably mounting said discs in fixed relation to each other to define the slot overlap;
   (d) means for mounting said discs in fixed relation to one of the orthotic members;
   (e) structure for pivotally traversing the slot overlap, said structure mounted in fixed relation to the other orthotic member; and
   (f) means for attaching said upper and lower orthotic members in operative position on a person.

17. The orthosis of claim 16 wherein said means for adjustably and removably mounting said discs in fixed relation to each other comprising a plurality of outwardly extending teeth spaced apart on the periphery of each of said discs and a plurality of corresponding teeth spaced apart around the periphery of an opening in a member that is fixed relative to said one of said orthotic members, said opening permitting said discs to be mounted therein.

18. The orthosis of claim 17 wherein said plurality of outwardly extending teeth extends around substantially the entire periphery of each disc.

19. The orthosis of claim 16 wherein said structure for traversing the slot overlap comprises a pin.

20. The orthosis of claim 16 wherein said other orthotic member has a joint end that comprises a clevis, the clevis dimensioned to permit said means for mounting said discs to be contained between said clevis.

21. The orthosis of claim 20 wherein one side of said clevis has an opening sufficiently large to permit insertion of said discs therethrough.

22. The orthosis of claim 21 wherein said structure for traversing the slot overlap comprises a pin.

23. The orthosis of claim 22 wherein said pin is rigidly mounted to a cover plate that is rigidly affixed and restrained from movement relative to said other orthotic member.

24. The orthosis of claim 23 wherein said cover plate has indicia on at least one side thereof to identify a range of pivotal movement of said joint.

25. The orthosis of claim 23 further comprising at least one slot located at the periphery of said cover plate and a corresponding raised portion adjacent said large clevis opening to prevent movement of said cover plate relative to said clevis.

26. The orthosis of claim 16 wherein the orthosis is a hip orthosis.

27. A method of adjusting an orthotic joint to provide a desired range of pivotal movement in said joint, wherein said joint comprises a pair of cooperating discs, each disc having a curved slot, at least a portion of each curved slot overlapping, the extent of slot overlap defining a permitted range of pivotal movement of said joint, structure for adjustably and removably mounting said discs in fixed relation to each other to define the slot overlap, structure for containing said discs in fixed relation to one of the orthotic members and structure for pivotally traversing the slot overlap, said structure mounted in fixed relation to the other orthotic member, comprising:

adjusting the relative relationship of said discs to provide a desired degree of slot overlap which corresponds to the desired range of pivotal movement of said joint; and installing said discs while in said relative relationship in said structure for containing said discs to provide the desired range of pivotal joint movement.

28. The method of claim 27 further comprising orienting said discs with respect to said structure for containing said discs to provide the desired orientation of said range of pivotal movement.

29. An orthotic joint for pivotally connecting two orthotic members comprising:

(a) a pair of cooperating discs, each having an axis of rotation, a periphery having at least one radially extending protrusion and, each disc having a curved slot radially spaced from the axis of rotation, at least a portion of each curved slot overlapping, the extent of slot overlap defining a permitted range of pivotal movement of said joint;

(b) a first orthotic member comprising an opening having a periphery with at least one recess complementary to said at least one protrusion of said discs and spaced apart along the periphery of the opening, to permit said discs to be adjustably and removably mounted in fixed relation to each other in said opening and to define the slot overlap in a fixed position in fixed relation to the first orthotic member; and (c) a protruding member for pivotally traversing the slot overlap, said protruding member mounted in fixed relation to the other orthotic member.

* * * * *

UNITED STATES PATENT AND TRADEMARK OFFICE
CERTIFICATE OF CORRECTION

PATENT NO. : 6,203,511 B1  Page 1 of 1
DATED : March 20, 2001
INVENTOR(S) : James A. Johnson and Robin W. McCall It is certified that error appears in the above-identified patent and that said Letters Patent is hereby corrected as shown below:

Column 1,
Lines 45 and 46, delete "there along" and insert therefor -- therealong --.

Column 3,
Line 36, delete "usefull" and insert therefor -- useful --.
Line 47, delete "usefill" and insert therefor -- useful --.

Column 5,
Line 18, delete "portion".
Line 32, delete "20" and insert therefor -- 26 --.
Line 48, after "extension" insert -- for --.

Signed and Sealed this

Eighteenth Day of December, 2001

Attest:

Attesting Officer

JAMES E. ROGAN
Director of the United States Patent and Trademark Office